United States Patent [19]
DuPont et al.

[11] 4,277,476
[45] Jul. 7, 1981

[54] DERIVATIVES OF FLUORENES AND FLUORANTHENES AND PROCESS FOR THEIR PREPARATION

[75] Inventors: Régis DuPont, Paris; Patrick Lardenois, Bourg-la-Reine; Claude Morel, Massy; Jonathan Frost, Palaiseau, all of France; Gabor I. Koletar, Berkeley Heights, N.J.

[73] Assignee: Synthelabo, Paris, France

[21] Appl. No.: 60,857

[22] Filed: Jul. 26, 1979

[30] Foreign Application Priority Data

Jul. 28, 1978 [FR] France ................. 78 22352
Jul. 28, 1978 [FR] France ................. 78 22353

[51] Int. Cl.³ .................... A01N 43/48; A61K 31/495
[52] U.S. Cl. ................................. 424/250; 544/247; 544/248
[58] Field of Search .............. 544/247, 248; 424/250

[56] References Cited

U.S. PATENT DOCUMENTS

| | | | |
|---|---|---|---|
| 2,556,574 | 6/1951 | Campbell et al. | 544/247 |
| 3,108,108 | 10/1963 | Schellhammer et al. | 544/247 X |
| 3,122,544 | 2/1964 | Osdene et al. | 544/247 |
| 3,470,181 | 9/1969 | Wei et al. | 544/248 |
| 3,631,046 | 12/1971 | Hardtmann | 544/247 |
| 3,669,969 | 6/1972 | Lunn | 544/247 |
| 3,963,720 | 6/1976 | Hardtmann | 544/247 |

FOREIGN PATENT DOCUMENTS 601299 7/1978 Switzerland .

*Primary Examiner*—Paul F. Shaver
*Attorney, Agent, or Firm*—Wegner & Bretschneider

[57] ABSTRACT

Derivatives of fluorenes and fluoranthenes, in the form of racemates or of enantiomers, of the formula (I)

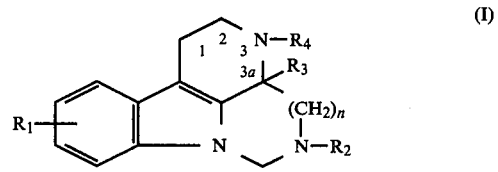

in which n is 1 or 2, $R_1$ is a hydrogen or halogen atom or an alkyl or alkoxy radical, $R_2$ is a hydrogen atom or an alkyl, cycloalkyl, cycloalkylalkyl, benzyl, halogenobenzyl, alkylbenzyl, alkoxybenzyl, acyl, alkoxycarbonyl or alkylaminocarbonyl radical, $R_3$ is a hydrogen atom or an alkyl radical, $R_4$ is a hydrogen atom or an alkyl, acyl or aroyl radical, the alkyl and alkoxy radicals or parts of radicals having from 1 to 4 carbon atoms and pharmaceutically acceptable acid addition salts thereof, are therapeutically valuable as anti-anoxia and psychotropic agents.

8 Claims, No Drawings

DERIVATIVES OF FLUORENES AND FLUORANTHENES AND PROCESS FOR THEIR PREPARATION

DESCRIPTION

The present invention relates to derivatives of octahydrotriazacycloheptafluorenes and of triazafluoroanthenes, in the form of racemates or of enantiomers, and their pharmaceutically acceptable acid addition salts. These derivatives are therapeutically valuable.

The fluorene and fluoranthene derivatives according to the invention are compounds of the general formula (I)

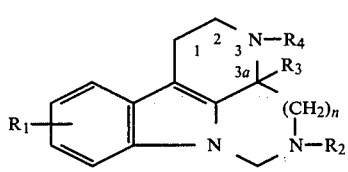

in which n is 1 or 2, $R_1$ is a hydrogen or halogen atom or an alkyl or alkoxy radical, $R_2$ is a hydrogen atom or an alkyl, cycloalkyl, cycloalkylalkyl, benzyl, halogenobenzyl, alkylbenzyl, alkoxybenzyl, acyl, alkoxycarbonyl or alkylaminocarbonyl radical, $R_3$ is a hydrogen atom or an alkyl radical, $R_4$ is a hydrogen atom or an alkyl, acyl or aroyl radical, and the alkyl and alkoxy radicals have from 1 to 4 carbon atoms, and their pharmaceutically acceptable acid addition salts. These derivatives are hereinafter referred to, for brevity, as the "compounds of the invention."

The above compounds possess an asymmetric carbon in the 3a-position. Their racemates and enantiomers form part of the invention.

A preferred class of compounds of the invention is those in which n is 1 or 2, $R_1$ is a fluorine or chlorine atom or a methyl or methoxy radical, $R_2$ is a hydrogen atom, an alkyl radical of 1 to 4 carbon atoms or a benzyl, cyclopropyl, acetyl, ethoxycarbonyl or methylaminocarbonyl radical, $R_3$ is a hydrogen atom or a methyl radical and $R_4$ is a hydrogen atom, an alkyl radical or an acetyl, propionyl, benzoyl or butyryl radical. Preferably n is 2.

Another preferred class of compounds of the invention is those in which n is 2, $R_1$ is a hydrogen atom or a 10-methoxy radical, $R_2$ is a methyl, cyclopropyl or benzyl radical, $R_3$ is a hydrogen atom and $R_4$ is an acetyl, benzoyl, ethyl or propyl group or a hydrogen atom.

Two specifically preferred compounds of the invention are 3-acetyl-1,2,3,3a,4,5,6,7-octahydro-3,6,7a-triazacyclohepta[j,k]fluorene and its 10-methoxy derivative.

The invention provides a process for the preparation of a compound of the invention in which $R_2$ is alkyl, cycloalkyl, cycloalkylalkyl, benzyl or substituted benzyl and $R_4$ is a hydrogen atom which comprises acidifying a compound of formula (VII)

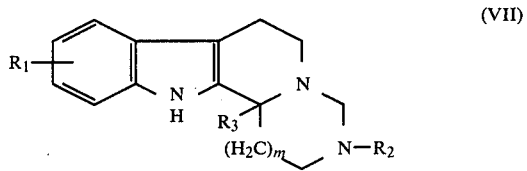

in which $R_1$, $R_2$ and $R_3$ have the meanings given above and m is 0 or 1, to effect a molecular rearrangement.

The compounds (I) in which $R_4$ is other than H can be prepared from the compounds (I) in which $R_4$ is H (where appropriate without isolating the latter) by direct alkylation or acylation. The compounds (I) for which $R_4$ is an acyl radical can be reduced to the compounds (I) for which $R_4$ is an alkyl radical.

The compounds (I) in which $R_2$ is H can be obtained from the compounds (I) in which $R_2$ is benzyl by debenzylation.

The compounds (I) in which $R_2$ is (i) an acyl, (ii) an alkylaminocarbonyl or (iii) an alkoxycarbonyl radical can be obtained from the corresponding compounds (I), in which $R_2$ is the benzyl radical, by debenzylation, which can be carried out by catalytic hydrogenolysis, e.g. using palladium on charcoal, under a hydrogen pressure of e.g. 3 to 4 kg/cm$^2$, followed by reaction of the compound thus obtained (in which $R_2$ is presumably hydrogen) with a compound which carries the $R_2$ group, i.e. (i) acid anhydride or acid chloride, the acid being of formula $R_5COOH$, an alkyl chloroformate $ClCOOR_5$ or an alkyl isocyanate $R_5NCO$, ($R_5$ being an alkyl radical).

A compound of formula (I) obtained as a free base can be converted into a pharmaceutically acceptable acid addition salt. A method known per se can be used.

The starting compounds (VII), in the form of racemates or of enantiomers, are new, with the exception of compounds in which simultaneously m=1, $R_1$=H or 9-bromo, $R_2$=CH$_3$ and $R_3$=H. The new compounds form part of the present invention.

The compounds (VII) for which m=0

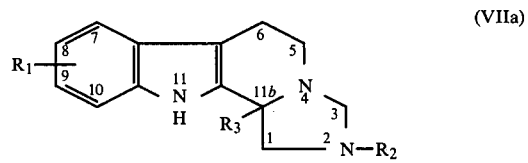

have an asymmetric carbon in the 11b-position.

The compounds (VII) in which m=1

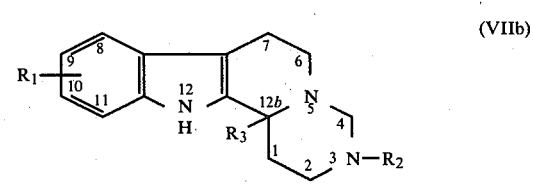

have an asymmetric carbon in the 12b-position.

The compounds (VII) can be prepared from a compound of the formula (II)

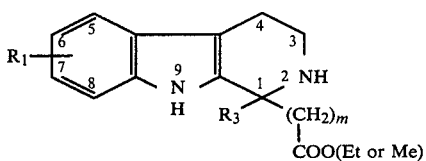

in which $R_1$, $R_3$ and m have the same meanings as above.

The invention also includes two processes for preparing the compounds (VII) from these starting products (II). These processes are illustrated by diagrams 1 and 2 which follow. In these diagrams, $R_2$ is an optionally substituted alkyl, cycloalkyl, cycloalkylalkyl or benzyl radical.

Diagram 1

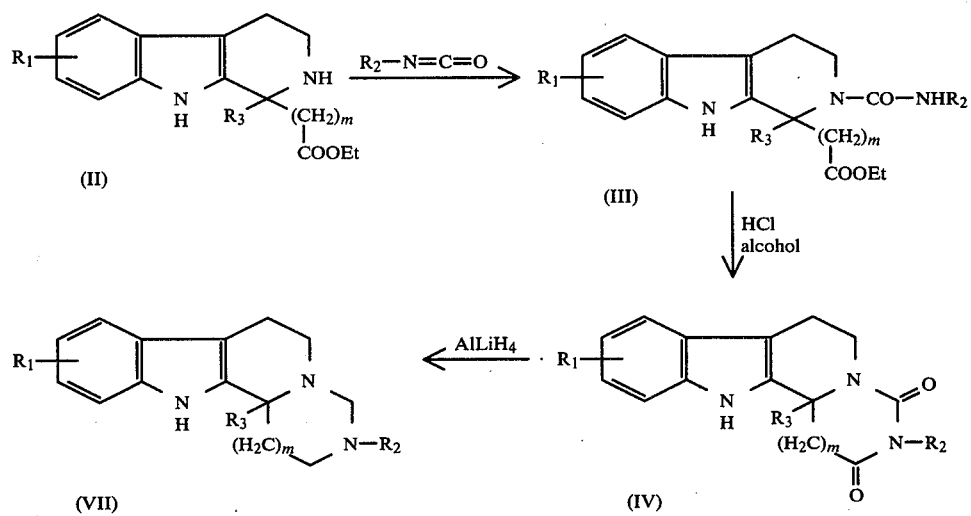

Diagram 2

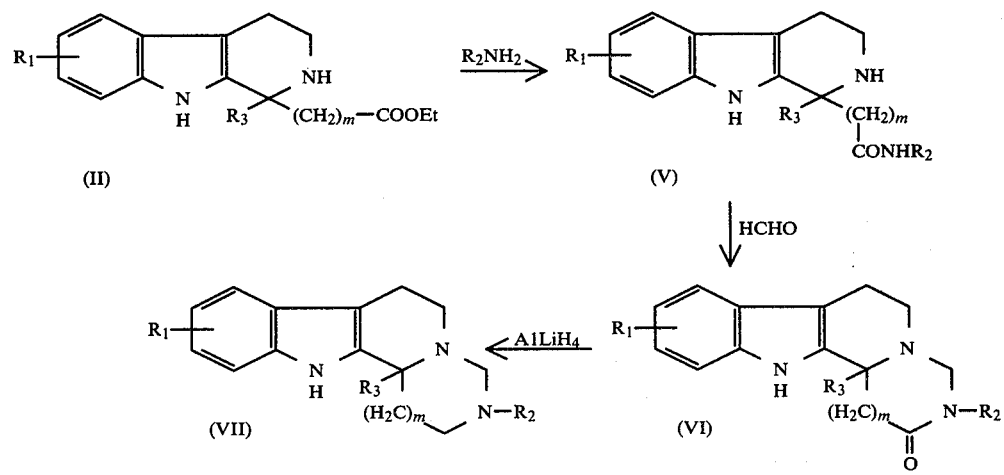

According to the process of diagram 1, the compounds (VII) are prepared from the compounds (II) in the form of bases, by reaction with an isocyanate of the formula $R_2—N=C=O$, in a neutral solvent such as cyclohexane or methylene chloride, at a temperature varying between ambient temperature and the boiling point of the solvent, the resulting compound (III) is then cyclised by means of hydrochloric acid in an alcoholic medium, at the boiling point of the alcohol, and finally the resulting compound (IV) is reduced to a compound (VIII) by means of lithium aluminium hydride in a solvent such as dioxane or tetrahydrofurane, at the boiling point of the solvent.

If $R_2=H$, the starting compound (II) is reacted, in the form of a salt (for example the hydrochloride), with sodium isocyanate in water at 50° C.

The resulting compounds (IV) in which $R_2$ is H can then give compounds (IV) in which $R_2$ is other than H, by direct substitution at the nitrogen (by alkylation and the like).

According to the process of diagram 2, the compound (II) is reacted with an amine of the formula $R_2NH_2$, using the amine itself as a solvent or working in a solvent such as an alcohol, at a temperature ranging from ambient temperature to 100° C., the resulting compound (V) is then cyclised by means of a 30% strength formaldehyde solution in water, and finally the compound (VI) is reduced by means of lithium aluminium hydride in a solvent such as dioxane or tetrahydrofurane at the boiling point of the solvent.

The starting compounds (II) are obtained as follows:

The starting compounds (II) in which $R_3$=alkyl can be prepared from substituted or unsubstituted tryptamine in accordance with the following scheme:

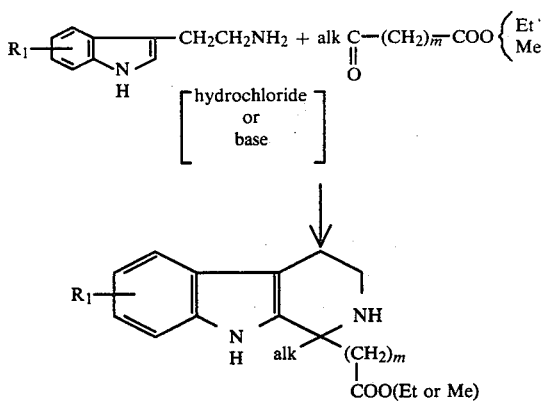

This reaction is described in the literature.

The starting compounds (II) in which $R_3=H$ and $m=1$ can be obtained from the hydrochloride of substituted or unsubstituted tryptamine, in accordance with the following scheme:

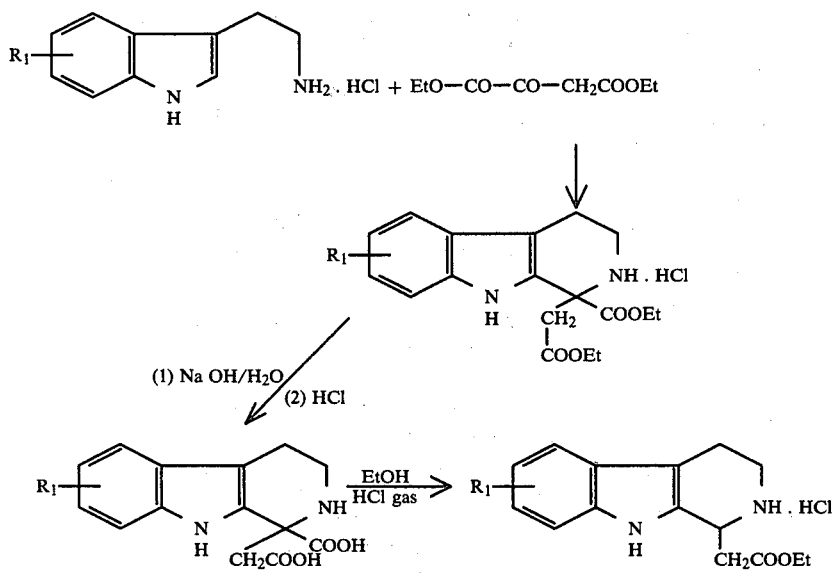

One method of preparation is as follows, for $R_1=H$.

1. A suspension of 115 g (0.55 mol) of sodium diethyloxaloacetate in 500 cm³ of EtOH is prepared. 50 cm³ of HCl of density 1.18 (representing 0.55 mol) are slowly added thereto. The resulting suspension is added, in an amount of ⅓ of its total volume, to a suspension of 98.2 g (0.5 mol) of tryptamine hydrochloride in 500 cm³ of boiling EtOH. Refluxing is continued, with stirring, for 2 hours, after which the second ⅓ of the suspension is introduced followed, after a further 2 hours' refluxing, by the last ⅓. About 700 cm³ of EtOH are distilled and the mixture is allowed to cool overnight. The crystalline mass is filtered off, washed with water (4×100 cm³) to remove NaCl and then washed with acetone.

After drying, the desired product is obtained, melting, with decomposition, at 230° C.

2. A suspension of 67.8 g of the diester obtained above in 700 cm³ of water containing 70 g of sodium hydroxide is heated to the boil for 48 hours. After it has cooled, 200 cm³ of HCl (d=1.19) are added. A precipitate forms, and is stirred for 1 hour. It is then filtered off, washed repeatedly with water, then washed with acetone and finally washed with ether.

3. 25 g of the above diacid are suspended in 180 cm³ of EtOH. The suspension is saturated with HCl gas, whilst stirring. The temperature rise is accompanied by complete solution. The mixture is heated overnight to keep it refluxing. After cooling, the product is filtered off and washed with EtOH and then with ether. White crystals of ethyl 2,3,4,9-tetrahydro-1H-pyrido[3,4-b]indole-1-acetate are obtained in the form of the hydrochloride.

Melting point=260° C.

The starting compound (II), in which $R_3=H$ and $m=0$ with $R_1=H$ is described in the literature (Z. J. Vejdelek and colleagues, J. of Med. and Pharm. Chem. Vol. 3, No. 3 (1961), pages 427–440).

The examples which follow illustrate the invention. The micro-analyses and the IR and NMR spectra confirm the structure of the compounds.

EXAMPLE 1

6-Methyl-1,2,3,3a,4,5,6,7-octahydro-3,6,7a-triaza-cyclohepta[j,k]fluorene

[$n=2$, $R_1=H$, $R_2=CH_3$, $R_3=H$, $R_4=H$]

1. Ethyl 2-carbamyl-2,3,4,9-tetrahydro-pyrido[3,4-b]indole-1-acetate.

26 g (0.088 mol) of ethyl 2,3,4,9-tetrahydro-1H-pyrido[3,4b]indole-1-acetate hydrochloride (starting compound II) are dissolved in 1 liter of hot water. The pH must be 4–5. When the reaction mixture is at 50° C., a solution of 8.7 g (0.13 mol) of sodium cyanate in 150 cm³ of water is added. The reaction mixture is kept at 50° C., with stirring. It is stirred at 50° C. for 4 hours and then is left to stand overnight at ambient temperature. The supernatant liquor is drawn off. 200 cm³ of ether are added, the mixture is stirred, the ether solution is then drawn off and the same operation is recommenced. The expected product is very soluble in ether. The ether extracts are combined and washed with slightly acidified water to remove traces of the starting product and then with water. They are dried over Na₂SO₄ and the solvent is evaporated. An oil is obtained, which turns to a froth on more thorough drying. The product is used in the form in which it is obtained for the next stage.

2.
1,2,3,4,6,7,12,12b-Octahydro-pyrimido[1',6':1,2-]pyrido[3,4-b]indole-2,4-dione 11.1 g of the preceding compound are dissolved in 250 cm³ of refluxing ethanol. At this temperature, a saturated solution of HCl gas in 55 cm³ of ethanol is added. This mixture is kept at the reflux temperature for 5 hours and is then left to stand overnight at ambient temperature. The product is filtered off and washed with EtOH and then with ether, and is dried. A product which is very insoluble in organic solvents is obtained. After recrystallisation from dimethylformamide, the product melts at 365° C.

3.
3-Methyl-1,2,3,4,6,7,12,12b-octahydro-pyrimido[1',6':1,2]pyrido[3,4-b]indole-2,4-dione 1.5 g (0.031 mol) of sodium hydride in the form of a 50% strength dispersion in oil are added to a solution of 8 g (0.031 mol) of the preceding compound in 300 cm³ of dimethylformamide. The mixture is stirred for 1 hour 30 minutes in the absence of moisture, 4.5 g (0.031 mol) of methyl iodide are then added and the reaction mixture is left overnight at ambient temperature, with constant stirring.

The inorganic residue is filtered off and the filtrate is then evaporated. The residue is taken up in water, which causes it to solidify to a white solid. The latter is recrystallised from ethanol. The pure compound, obtained after recrystallisation from methyl ethyl ketone, melts at 246°–248° C.

4.
3-Methyl-1,2,3,4,6,7,12,12b-octahydro-pyrimido[1',6':1,2]pyrido[3,4-b]indole A suspension of 4 g of the compound obtained under 3., in 80 cm³ of dioxane, is added dropwise, over 30 minutes, to a boiling suspension of 4 g of LiAlH₄ in 80 cm³ of dioxane. Refluxing is continued for 1 hour after the end of the addition. After cooling, the excess hydride is destroyed with a small amount of water. The mixture is filtered to remove the inorganic precipitate and the latter is washed repeatedly with ether. The organic filtrate is dried over Na₂SO₄ and then evaporated. The oil obtained is purified by passing it over a column of silica gel (100 g), using a 4/1 chloroform/methanol mixture. Trituration in ethyl acetate gives the desired compound, which after recrystallisation melts at 168° C.

5.
6-Methyl-1,2,3,3a,4,5,6,7-octahydro-3,6,7a-triazacyclohepta[j,k]fluorene A solution of 11.1 g of 3-methyl-1,2,3,4,6,7,12,12b-octahydro-pyrimido[1',6':1,2]pyrido[3,4-b]indole in 100 cm³ of methanol is stirred and 15 cm³ of methanol saturated with hydrochloric acid are added. The solution is stirred overnight at the temperature of the laboratory. It is then diluted with ether and filtered, the solid is brought into contact with NH₄OH, ethyl acetate is added, and the organic phase is decanted, washed with water and dried over Na₂SO₄. The solvent is evaporated. A yellow solid residue is obtained, which is triturated in ether and filtered off.

Melting point = 108°–109° C. (after recrystallisation from petroleum ether).

EXAMPLE 2
3-Acetyl-6-methyl-1,2,3,3a,4,5,6,7-octahydro-3,6,7a-triaza-cyclohepta[j,k]fluorene.

[n = 2, R₁ = H, R₂ = CH₃, R₃ = H, R₄ = CH₃CO]

5 g of 6-methyl-1,2,3,3a,4,5,6,7-octahydro-3,6,7a-triaza-cyclohepta[j k]fluorene (compound I, n = 2, R₂ = CH₃, R₁ = R₃ = R₄ = H) are rendered alkaline with NaHCO₃ and the free base is extracted with CHCl₃. The chloroform extracts are evaporated, the solid obtained is dissolved in 10 ml of pyridine and 6 ml of acetic anhydride are added. The reaction mixture is stirred for 15 minutes at ambient temperature and is then heated to the reflux temperature to complete the reaction. The cooled reaction mixture is poured into water (100 ml) and is extracted with chloroform.

After evaporation of the chloroform extracts, an oil is obtained, which when triturated in ethanol gives a solid. After recrystallisation from ethanol, the product melts at 184° C.

EXAMPLE 3
3-Acetyl-10-methoxy-6-methyl-1,2,3,3a,4,5,6,7-octahydro-3,6,7a-triaza-cyclohepta[j,k]fluorene.

[n = 2, R₁ = 10—CH₃O, R₂ = H, R₄ = CH₃CO]

1. Ethyl 1H-pyrido[3,4-b]6-methyl-2,3,4,9-tetrahydroindole-1-acetate 20 g of 5-methoxy-tryptamine hydrochloride and 100 ml of ethanol are introduced into a flask and heated to the reflux temperature. 20.3 g of sodium diethyl-oxaloacetate and 100 ml of ethanol are introduced into an Erlenmeyer flask. 8 ml of concentrated hydrochloric acid are added and the mixture is stirred for 10 minutes. The suspension of the oxalate in ethanol is introduced into the tryptamine suspension and the mixture is heated to the reflux temperature for 7 hours and is then left to cool overnight. The solvent is driven off and the residue is rendered alkaline with ammonia. The mixture is extracted 3 times with 300 ml of chloroform. The chloroform is driven off and an oil is obtained, which is chromatographed over silica. After elution with a 2/8 mixture of EtOH/CHCl₃, an oil is obtained, which is crystallised from petroleum ether. After recrystallisation, the product melts at 100° C.

150 ml of a 10% strength solution of NaOH are added and the mixture is heated to the reflux temperature for 20 hours. It is then acidified with 50 ml of concentrated hydrochloric acid and filtered. A mixture of ethanol (250 ml) and concentrated sulphuric acid (20 ml) is added to the compound obtained. The mixture is heated to the reflux temperature for 4 hours. After it has cooled, the residue is rendered alkaline and the mixture is extracted with chloroform. After evaporation of the solvent, and chromatography of the resulting oil on silica, a compound is obtained, of which the maleate is prepared in ethanol.

Melting point = 181° C.

2.
N-Methyl-[6-methoxy-2,3,4,9-tetrahydro-1H-pyrido[3-4b]indole]-1-acetamide.

15 g of the compound obtained under 1 (as the base) are introduced into a bomb tube and 500 ml of a 33% strength methylamine solution in ethanol are added. The mixture is heated at 100° C. for 7 hours and left to cool overnight. The ethanol is driven off and a brown solid is obtained, which is crystallised from ethanol. Melting point—190° C.

3.
9-Methoxy-3-methyl-1,2,3,4,6,7,12,12b-octahydro-2-oxopyrimido[1',6':1,2]pyrido[3,4-b]indole 10.3 g of the compound obtained under 2 are introduced into an Erlenmeyer flask. 100 ml of ethanol and 10 ml of a 30% strength formaldehyde solution in water are added. The mixture is stirred for 2 hours. The solvent is driven off and a white solid is obtained, which is recrystallised from ethanol.

Melting point=224° C.

4.
9-Methoxy-3-methyl-1,2,3,4,6,7,12,12b-octahydropyrimido[1',6':1,2]pyrido[3,4-b]indole.

4 g of LiAlH$_4$ and 100 ml of THF are introduced into a flask. The mixture is heated to the reflux temperature and 7.5 g of the compound obtained under 3, dissolved in 100 ml of THF, are added in the course of 10 minutes. The mixture is kept at the reflux temperature for 1 hour. It is then left to cool and water and sodium hydroxide are added. The mixture is filtered and the solvent is driven off. The white solid, when recrystallised from ethyl acetate, melts at 199°–200° C.

5.
3-Acetyl-10-methoxy-6-methyl-1,2,3,3a,4,5,6,7-octahydro-3,6,7a-triaza-cyclohepta[j,k]fluorene.

20 ml of pyridine and 3.3 ml of acetic anhydride are added to the compound obtained under 4. The mixture is stirred at ambient temperature for 1 hour. The pyridine is driven off and a solid is obtained, which is recrystallised from ethanol.

Melting point=165° C.

EXAMPLE 4
3-Ethyl-6-methyl-1,2,3,3a,4,5,6,7-octahydro-3,6,7a-triaza-cyclohepta[j k]fluorene.

[n=2, R$_1$=H, R$_2$=CH$_3$, R$_3$=H, R$_4$=C$_2$H$_5$]

2.5 g of 3-acetyl-6-methyl-1,2,3,3a,4,5,6,7-octahydro-3,6,7a-triaza-cyclohepta[j,k]fluorene (compound I, R$_1$=H, R$_2$=CH$_3$, R$_3$=H, R$_4$=CH$_3$CO, n=2) are stirred with 2.4 g of LiAlH$_4$ in 60 ml of dioxane at ambient temperature for 10 minutes. The mixture is then slowly raised to the reflux temperature and is maintained thereat for 1 hour. The reaction mixture is then cooled and the excess LiAlH$_4$ is destroyed. The inorganic precipitate is filtered off and the filtrate is then evaporated. An oil is obtained, which is purified by passing over an SiO$_2$ column. Elution is carried out with a 2/8 EtOH/CHCl$_3$ mixture. After recrystallisation from petroleum ether, the product melts at 78°–79° C.

EXAMPLE 5
3-Benzyl-1,2,3,3a,4,5,6,7-octahydro-3,6,7a-triazacyclohepta[j k]fluorene

[n=2, R$_1$=H, R$_2$=C$_6$H$_5$CH$_2$, R$_3$=H, R$_4$=H]

1.
N-Benzyl-[2,3,4,9-tetrahydro-1H-pyrido[3,4-b]indole]-1-acetamide.

The base is liberated from 60 g (0.20 mol) of ethyl 2,3,4,9-tetrahydro-1H-pyrido[3,4-b]indole-1-acetate hydrochloride in a mixture of water plus ammonia/methylene chloride. After separating the phases and drying the organic phase over Na$_2$SO$_4$, the solvent is evaporated. The resulting gum is dissolved in 200 cm$^3$ of benzylamine. This solution is heated for 42 hours at 110°–120° C., with stirring. The benzylamine is removed at this temperature by vacuum distillation. After cooling, crystallisation starts and the material then sets solid. It is triturated in ether and the crystals are filtered off and washed with ether. The desired compound is obtained and after recrystallisation from ethyl acetate melts at 160° C.

2.
3-Benzyl-1,2,3,4,6,7,12,12b-octahydro-2-oxopyrimido[1',6':1,2]pyrido[3,4-b]indole.

A suspension of 43.4 g (0.135 mol) of the preceding compound in 650 cm$^3$ of ethanol is warmed slightly, until the material has dissolved. 40 cm$^3$ of formaldehyde as a 30% strength solution in water are added and the mixture is stirred at 40° C. for 2 hours and then overnight at ambient temperature. Evaporation of the solvent gives a paste which solidifies slowly. When this is triturated in ether, fine crystals are obtained, which are filtered off, washed with water and dried. After recrystallisation from ethanol, the compound melts at 198°–200° C.

3.
3-Benzyl-1,2,3,4,6,7,12,12b-octahydropyrimido[1',6':1,2]pyrido[3,4-b]indole.

A solution of 24.2 g (0.073 mol) of the preceding compound in 400 cm$^3$ of tetrahydrofurane is added dropwise to a boiling suspension of 12 g (0.3 mol) of LiAlH$_4$ in 120 cm$^3$ of tetrahydrofurane. Refluxing is continued for 1 hour after the end of the addition. After cooling, the excess hydride is destroyed.

The inorganic residue is filtered off and washed with ether. The filtrate is dried over Na$_2$SO$_4$ and the solvent is evaporated. A white crystalline mass is obtained, which is triturated in diisopropyl ether and then filtered off. After recrystallisation from ethyl acetate, the product melts at 158° C.

4.
6-Benzyl-1,2,3,3a,4,5,6,7-octahydro-3,6,7a-triazacyclohepta[j,k]fluorene.

51.6 g of the compound obtained above under 3., in 500 cm$^3$ of ethanol saturated with HCl gas, are stirred for 48 hours at ambient temperature. The precipitate formed is filtered off on a frit and washed with ethanol and then with ether. The product is dried in a vacuum oven at 50° C. 62.8 g of the dihydrochloride of the desired compound are obtained.

The base, after liberation from its salt and recrystallisation from isopropanol, melts at 129° C.

EXAMPLE 6
3-Acetyl-6-benzyl-1,2,3,3a,4,5,6,7-octahydro-3,6,7a-triaza-cyclohepta[j k]fluorene.

[n=2, $R_1$=H, $R_2$=$C_6H_5CH_2$, $R_3$=H, $R_4$=$CH_3CO$]

30 g (0.076 mol) of 6-benzyl-1,2,3,3a,4,5,6,7-octahydro-3,6,7a-triaza-cyclohepta[j,k]fluorene (compound (I), n=2, $R_1$=H, $R_2$=$C_6H_5CH_2$, $R_3$=H) are dissolved in 100 cm$^3$ of pyridine and 30 cm$^3$ of acetic anhydride are then added. The mixture is stirred overnight at ambient temperature. The crystalline mass is filtered off. The filtrate is evaporated in vacuo and the residue is then taken up in methylene chloride. The crystalline mass is dissolved in methylene chloride. The organic fractions are combined, washed with water, dried over $Na_2SO_4$ and then evaporated in vacuo. The residue obtained is freed from traces of pyridine by evaporation in vacuo in the presence of toluene. The solid residue is triturated with ether and then filtered off. After washing with ether and drying, the acetylated compound is obtained. After recrystallisation from ethyl acetate, the compound melts at 165°–166° C.

EXAMPLE 7
3-Acetyl-6-ethoxycarbonyl-1,2,3,3a,4,5,6,7-octahydro-3,6,7a-triaza-cyclohepta[j k]fluorene

[n=2, $R_1$=H, $R_2$=$COOC_2H_5$, $R_3$=H, $R_4$=$CH_3CO$]

1. A mixture of 20 g of the compound obtained in Example 6 in 250 cm$^3$ of acetic acid and of 2 g of 10% strength palladium on charcoal is subjected to hydrogenolysis at ambient temperature for 24 hours under a hydrogen pressure of 3.5 kg/cm$^2$. The mixture is filtered to remove the catalyst. The filtrate is evaporated in vacuo, then diluted with water, neutralised with dilute ammonia and then extracted with ethyl acetate. After drying the extract over $Na_2SO_4$, the solvent is evaporated. The oily residue is dissolved in 20 cm$^3$ of chloroform and the solution is left in a refrigerator for 48 hours. The compound obtained is filtered off. After recrystallisation from ethyl acetate, it melts at 138°–140° C.

2. 10 g of this compound are suspended in a mixture of 150 cm$^3$ of ether and 150 cm$^3$ of water containing 2.3 g of potassium hydroxide pellets. 3.2 cm$^3$ of ethyl chloroformate are added whilst stirring and the mixture is stirred for 5 hours. Ethyl acetate is added until the precipitate has dissolved completely. The organic phase is separated off, washed with water, dried over $Na_2SO_4$ and then evaporated. The white solid obtained is triturated in ether and then filtered off and dried. After recrystallisation from ethanol, the compound melts at 195°–196° C.

EXAMPLE 8
3-Acetyl-3a-methyl-5-methyl-9-fluoro-2,3,3a,4,5,6-hexahydro-3,5,6a-triaza-fluoranthene

[n=1, $R_1$=F-9, $R_2$=$CH_3$, $R_3$=$CH_3$, $R_4$=$CH_3CO$]

1.
1-Methylaminocarbonyl-1-methyl-9-fluoro-2,3,4,9-tetrahydro-1H-pyrido[3,4-b]indole 30 g (0.139 mol) of 5-fluoro-tryptamine hydrochloride are suspended in 450 ml of methanol. 15 ml of methyl pyruvate are added. The mixture is stirred at ambient temperature for 5 days. The solvent is driven off on a rotary evaporator. The residue is taken up in a water/ethyl acetate mixture and rendered alkaline with a N sodium hydroxide solution. The organic phase is decanted, washed, dried and then evaporated. The crystalline residue is taken up in 20 ml of $CH_2Cl_2$. This mixture is stirred for 15 minutes in an ice bath and the precipitate is then filtered off and recrystallised from toluene. Melting point=177° C.

3.2 g (0.0122 mol) of the compound obtained above and 50 ml of a 33% strength solution of methylamine in ethanol are introduced into a flask. The mixture is stirred at ambient temperature for 24 hours. The precipitate is then filtered off and recrystallised from n-propanol. Melting point=238° C.

2.
2-Methyl-11b-methyl-8-fluoro-2,3,5,6,11,11b-hexahydro-1-oxo-imidazo[1',5':1,2]pyrido[3,4-b]indole 5.4 g (0.0206 mol) of the compound obtained under 1. are introduced into 100 ml of ethanol. 1.5 g of potassium hydroxide pellets followed by 15 ml of a 30% strength solution of formaldehyde are added. The mixture is heated on an oil bath at 70° C. for 24 hours. The ethanol solution is reduced to 20 ml and the precipitate is filtered off. After recrystallisation from ethanol, it melts at 223° C.

3.
2-Methyl-11b-methyl-8-fluoro-2,3,5,6,11,11b-hexahydroimidazo[1',5':1,2]pyrido[3,4-b]indole.

2.85 g (0.0104 mol) of the compound obtained under 2., dissolved in anhydrous tetrahydrofurane (40 ml), are added to a suspension of 1 g of LiAlH$_4$ in 25 ml of anhydrous THF. The mixture is heated to the reflux temperature for 2 hours and then cooled, and the excess hydride is destroyed. After evaporating the extraction solvent, a crystalline residue is obtained. Melting point=203° C.

4.
3-Acetyl-3a-methyl-5-methyl-9-fluoro-2,3,3a,4,5,6-hexahydro-3,5,6a-triaza-fluoranthene 2.65 g (0.102 mol) of the compound obtained under 3. are treated with 30 ml of a 10% strength solution of nitromethane in sulphuric acid. The mixture is stirred at ambient temperature for 48 hours. The solvent is then driven off on a rotary evaporator. The residue is taken up with ice, ethyl acetate is added and the mixture is rendered alkaline with ammonia. The organic phase is decanted and the solvent is evaporated. The residue is taken up in 25 ml of pyridine and 1 ml of acetic anhydride is added. This mixture is stirred at ambient temperature for 2 hours. The solution is then evaporated in vacuo on a water bath, and the residue is taken up with ice. It is treated with an aqueous N NaOH solution and the mixture is extracted with ethyl acetate. The organic phase is washed, dried and evaporated, and the residue is recrystallised from diisopropyl ether.

Melting point=110° C.

The compounds of the invention prepared by way of examples are shown in the table which follows:

TABLE I

Compounds of the formulae:

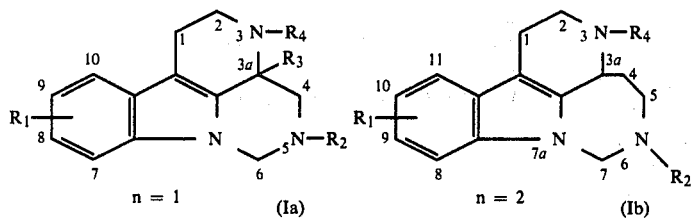

| Compound No | n | $R_1$ | $R_2$ | $R_3$ | $R_4$ | Melting point |
|---|---|---|---|---|---|---|
| 1 | 2 | H | $CH_3$ | H | H | 108-9 |
| 2 | 2 | H | $C_2H_5$ | H | H | 240-2 (dec) |
| 3 | 2 | H | $nC_3H_7$ | H | H | 109 |
| 4 | 2 | H | $nC_4H_9$ | H | H | 74 |
| 5 | 2 | H | $CH_3$ | H | $CH_3$ | 184 |
| 6 | 2 | Cl-10 | $CH_3$ | H | $CH_3$ | 151 |
| 7 | 2 | F-10 | $CH_3$ | H | $CH_3$ | 188 |
| 8 | 2 | $CH_3$-10 | $CH_3$ | H | $CH_3$ | 174 |
| 9 | 2 | H | $CH_3$ | H | $C_2H_5$ | 136.5 |
| 10 | 2 | H | ▷ | H | H | 137 |
| 11 | 2 | H | $CH_3$ | H | $C_2H_5$ | 79 |
| 12 | 2 | $CH_3$-10 | $CH_3$ | H | $C_2H_5$ | oil |
| 13 | 2 | Cl-10 | $CH_3$ | H | $C_2H_5$ | 121 |
| 14 | 2 | H | $CH_3$ | H | $C_6H_5$ | 168-9 |
| 15 | 2 | H | $CH_3$ | $CH_3$ | $CH_3$ | 142 |
| 16 | 2 | H | $C_6H_5CH_2$ | H | H | 129 |
| 17 | 2 | H | $CH_3$ | H | $C_3H_7$ | oil |
| 18 | 1 | H | $CH_3$ | $CH_3$ | $CH_3$ | 145 |
| 19 | 1 | F-9 | $CH_3$ | $CH_3$ | $CH_3$ | 110 |
| 20 | 2 | H | ▷ | H | $COCH_3$ | 187-8 |
| 21 | 2 | H | $CH_3$ | H | $COCH_2CH_2CH_3$ | 108 |
| 22 | 2 | H | $C_6H_5CH_2$ | H | $COCH_3$ | 165-6 |
| 23 | 2 | H | H | H | $COCH_3$ | 138-140 |
| 24 | 2 | H | $CH_3$ | H | $CH_2CH_2CH_2CH_3$ | oil |
| 25 | 2 | H | $C_6H_5CH_2$ | H | $CH_2CH_3$ | 100-101 |
| 26 | 2 | H | $C_6H_5CH_2$ | H | $COCH_2CH_3$ | 133-4 |
| 27 | 2 | H | $COCH_3$ | H | $COCH_3$ | 207-8 |
| 28 | 2 | H | $COOC_2H_5$ | H | $COCH_3$ | 195-6 |
| 29 | 2 | $CH_3O$-10 | $CH_3$ | H | $COCH_3$ | 165 |
| 30 | 2 | H | $CONHCH_3$ | H | $COCH_3$ | >300 |

The intermediate compounds (VII) are shown in Table (II) below:

TABLE II

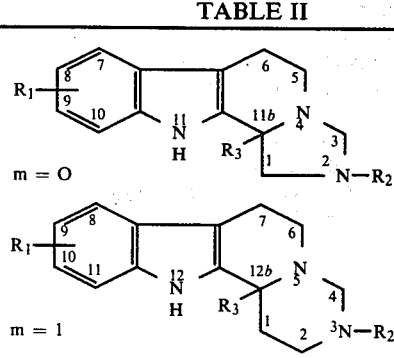

| Compound No | m | $R_1$ | $R_2$ | $R_3$ | Melting point |
|---|---|---|---|---|---|
| 1 | 1 | Cl-9 | $CH_3$ | H | 218-9 |
| 2 | 1 | F-9 | $CH_3$ | H | 194 |
| 3 | 1 | $CH_3$-9 | $CH_3$ | H | 215 |
| 4 | 1 | H | $CH_3$ | H | 168 |
| 5 | 1 | H | $C_2H_5$ | H | — |
| 6 | 1 | H | $C_3H_7$ | H | — |
| 7 | 1 | H | $C_4H_9$ | H | — |
| 8 | 1 | H | ▷ | H | — |
| 9 | 1 | H | $C_6H_5CH_2$ | H | 158 |
| 10 | 1 | H | $CH_3$ | $CH_3$ | 200 |
| 11 | 0 | H | $CH_3$ | H | 209-211 |
| 12 | 0 | H | $CH_3$ | $CH_3$ | 195 |
| 13 | 0 | F-8 | $CH_3$ | $CH_3$ | 203 |
| 14 | 1 | $CH_3O$-9 | $CH_3$ | H | 199-200 |

The compounds of the invention were subjected to pharmacological tests.

The compounds proved active in the reduced pressure anoxia test in mice and have an effect on the duration of sleep induced by sodium 4-hydroxy-butyrate (GHB) in curarised rats.

REDUCED PRESSURE ANOXIA

Mice of strain CDL are kept in an atmosphere depleted in oxygen by setting up a partial vacuum (190 mm of mercury, corresponding to 5.25% of oxygen).

The survival time of the animals is noted. This time is increased by agents capable of assisting tissue oxygenation and in particular cerebral oxygenation. The compounds studies are administered intraperitoneally, at various doses, 10 minutes before the test. The percentage increases in the survival time relative to the values obtained with comparison animals are calculated. The mean active dose (MAD), namely the dose which increases the survival time by 100%, is determined graphically.

The MAD of the compounds of the invention varies from 10 to 30 mg/kg when administered intraperitoneally.

ACTION ON THE DURATION OF "SLEEP"

This action was determined from the influence of the compounds on the duration of the "sleep" induced by sodium 4-hydroxy-butyrate (GHB) in curarised rats under artificial respiration, the electrocorticographic activity in the rats being recorded by cortical electrodes.

The compounds of the invention reduce the total duration of the sleep by from −20 to −37%.

The pharmacological study of the compounds of the invention shows that they are active in the reduced pressure anoxia test on mice, whilst being only slightly toxic, and that they exert a significant waking action in the test concerning the "sleep" induced by sodium 4-hydroxy-butyrate.

The compounds of the invention, possessing both an anti-anoxia activity and a psychotropic activity, can be used in therapeutics for the treatment of vigilance disturbances, in particular for combating behaviour disturbances attributable to cerebral vascular damage and to cerebral sclerosis in geriatrics, as well as for the treatment of epileptic vertigo due to cranial traumatisms, and the treatment of states of depression.

Conveniently, pharmaceutical compositions can be formulated to contain the compounds of formula (I) and/or their salts as active principle, in association with a pharmaceutically acceptable excipient. The excipients will be chosen to be appropriate for the route of administration, in particular their oral or parenteral administration.

The methods of administration can be oral or parenteral.

The daily posology can range from 10 to 1,000 mg.

We claim:

1. A compound of the formula:

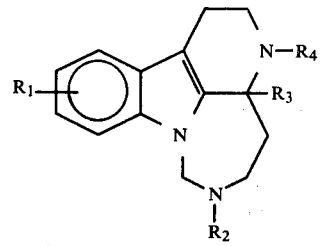

wherein $R_1$ is hydrogen, halogen, alkyl or alkoxy; $R_2$ is hydrogen, alkyl, cycloalkyl, cycloalkylalkyl, benzyl, halogenobenzyl, alkylbenzyl, alkoxybenzyl, acyl, alkoxycarbonyl or alkylaminocarbonyl; $R_3$ is hydrogen or alkyl; and $R_4$ is hydrogen, alkyl, acyl or aroyl; each alkyl and alkoxy having from 1 to 4 carbon atoms; or a pharmaceutically acceptable acid addition salt thereof.

2. A compound of claim 1, wherein $R_1$ is fluorine, chlorine, methyl or methoxy; $R_2$ is hydrogen, alkyl, benzyl, cyclopropyl, acetyl, ethoxycarbonyl or methylaminocarbonyl; $R_3$ is hydrogen, alkyl, acetyl, propionyl, butyryl or benzoyl.

3. A compound of claim 1 wherein $R_1$ is hydrogen or 10-methoxy; $R_2$ is methyl, cyclopropyl or benzyl; $R_3$ is hydrogen; and $R_4$ is hydrogen, acetyl, benzoyl, ethyl or propyl.

4. A compound according to claim 1 which is 3-acetyl-6-methyl-1,2,3,3a,4,5,6,7-octahydro-3,6,7a-triazacyclohepta [j,k]fluorene.

5. A compound according to claim 1 which is 3-acetyl-10-methoxy-6-methyl-1,2,3,3a,4,5,6,7-octahydro-3,6,7a-triazacyclohepta[j,k]fluorene.

6. A pharmaceutical composition comprising an effective amount of a compound claimed in claim 4, 5, 1, 2 or 3 in association with a pharmaceutically acceptable excipient therefor.

7. A method of providing a subject with an anti-anoxia effect which comprises administering to said patient an anti-anoxially effect amount of a compound of claim 4, 5, 1, 2 or 3.

8. A method of retarding depression which comprises administering to a subject an effective amount of a compound of claim 4, 5, 1, 2 or 3 to retard depression.

* * * * *